(12) United States Patent
Tai et al.

(10) Patent No.: US 10,008,443 B2
(45) Date of Patent: Jun. 26, 2018

(54) IMPLANT DEVICE

(71) Applicant: California Institute of Technology, Pasadena, CA (US)

(72) Inventors: Yu-Chong Tai, Pasadena, CA (US); Han-Chieh Chang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days. days.

(21) Appl. No.: 14/838,788

(22) Filed: Aug. 28, 2015

(65) Prior Publication Data

US 2015/0371929 A1   Dec. 24, 2015

Related U.S. Application Data

(63) Continuation-in-part of application No. 13/830,272, filed on Mar. 14, 2013, now Pat. No. 9,144,490.

(Continued)

(51) Int. Cl.
| | |
|---|---|
| *A61F 2/16* | (2006.01) |
| *H01B 13/00* | (2006.01) |
| *H01L 23/498* | (2006.01) |
| *H01L 21/48* | (2006.01) |
| *H01L 23/055* | (2006.01) |
| *H01L 21/02* | (2006.01) |
| *A61N 1/05* | (2006.01) |
| *A61N 1/36* | (2006.01) |

(Continued)

(52) U.S. Cl.
CPC .... *H01L 23/4985* (2013.01); *H01L 21/02002* (2013.01); *H01L 21/4846* (2013.01); *H01L 23/055* (2013.01); *H01L 23/49894* (2013.01); *A61N 1/0543* (2013.01); *A61N 1/36046* (2013.01); *A61N 5/0622* (2013.01); *H01L 23/10* (2013.01); *H01L 2924/0002* (2013.01); *H01M 2/026* (2013.01)

(58) Field of Classification Search
CPC ..... A61N 1/36046; A61N 1/0543; A61F 2/14; A61F 9/08; A61F 9/00727
See application file for complete search history.

(56) References Cited

U.S. PATENT DOCUMENTS

| | | | |
|---|---|---|---|
| 777,493 | A | 12/1904 | Burke |
| 5,178,957 | A | 1/1993 | Kolpe et al. |

(Continued)

FOREIGN PATENT DOCUMENTS

| | | |
|---|---|---|
| CN | 101398614 | 4/2009 |
| CN | 102355854 | 2/2012 |
| WO | 2010090706 A2 | 8/2010 |

OTHER PUBLICATIONS

International Search Report for corresponding PCT application PCT/US2013/031752 dated Jun. 28, 2013.

(Continued)

*Primary Examiner* — David H Willse
*Assistant Examiner* — Tiffany Shipmon
(74) *Attorney, Agent, or Firm* — Kilpatrick Townsend & Stockton LLP

(57) ABSTRACT

The invention provides chip packaging and processes for the assembly of retinal prosthesis devices. Advantageously, photo-patternable adhesive or epoxy such as photoresist is used as glue to attach a chip to the targeted thin-film (e.g., parylene) substrate so that the chip is used as an attachment to prevent delamination.

17 Claims, 19 Drawing Sheets

Related U.S. Application Data

(60) Provisional application No. 61/640,569, filed on Apr. 30, 2012.

(51) Int. Cl.
*A61N 5/06* (2006.01)
*H01M 2/02* (2006.01)
*H01L 23/10* (2006.01)

(56) References Cited

U.S. PATENT DOCUMENTS

| | | |
|---|---|---|
| 6,516,808 B2 | 2/2003 | Schulman et al. |
| 7,127,286 B2 | 10/2006 | Mech et al. |
| 7,211,103 B2 | 5/2007 | Greenberg et al. |
| 7,326,649 B2 | 2/2008 | Rodger et al. |
| 7,494,749 B2 | 2/2009 | Haines et al. |
| 7,774,931 B2 | 8/2010 | Tai et al. |
| 8,133,698 B2 | 3/2012 | Silver et al. |
| 8,423,143 B2 | 4/2013 | Bartic et al. |
| 2004/0106262 A1 | 6/2004 | Theiss et al. |
| 2004/0199235 A1 | 10/2004 | Younis et al. |
| 2005/0147898 A1 | 7/2005 | Haines |
| 2006/0138657 A1 | 6/2006 | Kushima et al. |
| 2007/0096281 A1 | 5/2007 | Greenberg et al. |
| 2007/0293749 A1* | 12/2007 | Zhou ............... A61N 1/0543 600/372 |
| 2008/0058895 A1 | 3/2008 | Ok et al. |
| 2009/0198293 A1 | 8/2009 | Cauller et al. |
| 2009/0228086 A1* | 9/2009 | Greenberg ........... A61N 1/0558 607/116 |
| 2010/0265680 A1* | 10/2010 | Tai ..................... A61B 5/0031 361/760 |
| 2011/0254171 A1 | 10/2011 | Guo et al. |
| 2012/0303118 A1 | 11/2012 | DeBoer et al. |
| 2013/0000119 A1 | 1/2013 | Tai et al. |
| 2013/0297019 A1 | 11/2013 | Tai et al. |

OTHER PUBLICATIONS

International Search Report for corresponding PCT application PCT/US2016/049034 dated Nov. 4, 2016 (7 pages).

Chang et al., "High density 256-channel chip integration with flexible parylene pocket", IEEE, 16th International Solid-State Sensors, Actuators and Microsystems Conference, Jun. 5-9, 2011, pp. 378-381.

Chang et al., "High yield packaging for high-density multi-channel chip integration on flexible parylene substrate", IEEE 25th International Conference on, Micro Electro Mechanical Systems, Jan. 29-Feb. 2, 2012, pp. 353-356.

Rodger et al., "Scalable High Lead-Count Parylene Package for Retinal Prostheses", Sensors and Actuators B, vol. 117, Issue 1, Sep. 12, 2006, pp. 107-114.

CN201380022588.4 , "Office Action", dated Aug. 29, 2017, 3 pages.

Declaration by Yu-Chong Tai and Han-Chieh Chang as filed in U.S. Appl. No. 13/830,272 dated Oct. 17, 2014 (6 pages).

* cited by examiner

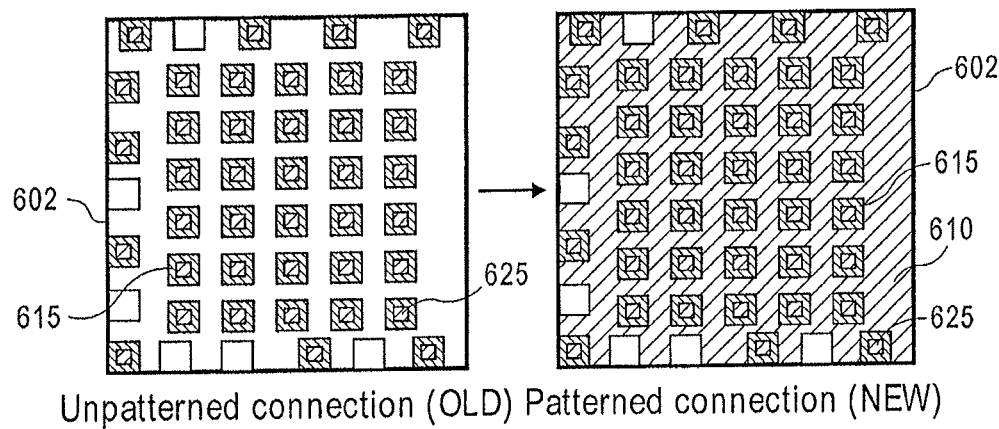
Unpatterned connection (OLD)  Patterned connection (NEW)
FIG. 6A  FIG. 6B
LEGEND
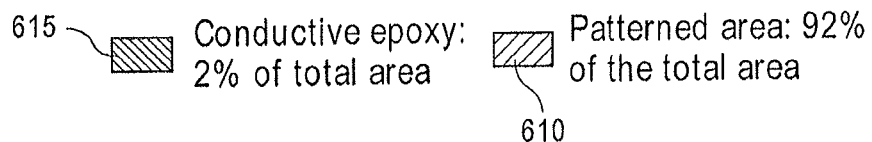

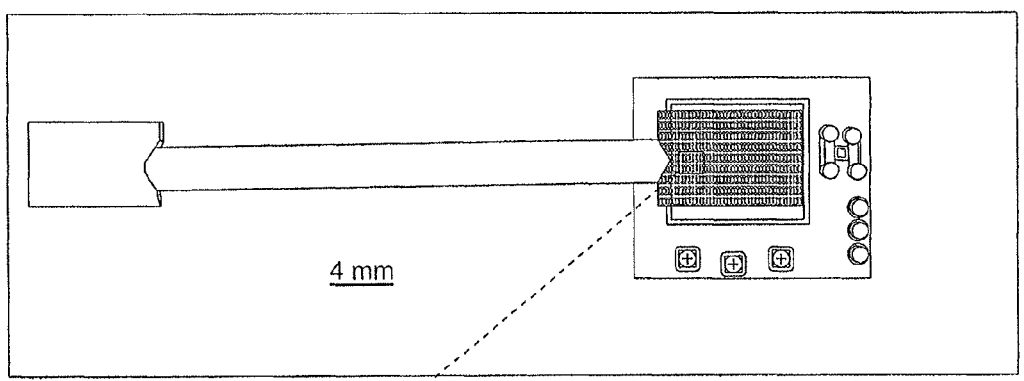
FIG. 13A
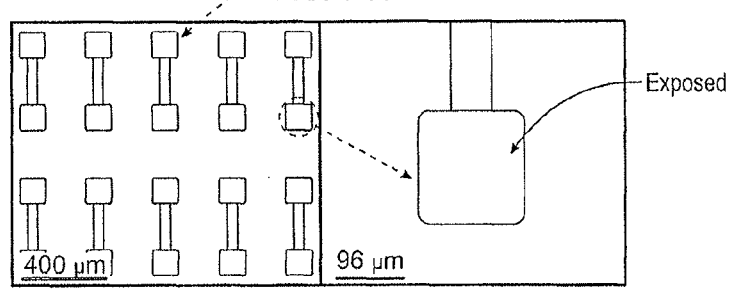
FIG. 13B     FIG. 13C

IMPLANT DEVICE

CROSS-REFERENCES TO RELATED APPLICATIONS

This application is a continuation-in-part of U.S. patent application Ser. No. 13/830,272, filed Mar. 14, 2013 (allowed), which application claims priority to U.S. Patent Application No. 61/640,569, filed Apr. 30, 2012, the disclosures of which are hereby incorporated by reference in their entirety for all purposes.

STATEMENT AS TO RIGHTS TO INVENTIONS MADE UNDER FEDERALLY SPONSORED RESEARCH OR DEVELOPMENT

This invention was made with government support under EEC0310723 awarded by the National Science Foundation. The government has certain rights in the invention.

FIELD OF INVENTION

This invention relates to biomedical implants in general and in particular to biomedical implants that employ a parylene substrate that allows the total connection and fabrication of a biomedical implant comprising semiconductor chips or other pre-manufactured electrical components such as transistors, resistors, capacitors or inductors.

BACKGROUND OF THE INVENTION

One of the biggest challenges that a prosthetic implant has to overcome is the reliable packaging of integrated circuit (IC) chips with bio-devices to withstand corrosive body fluids. This is especially true for complex neural implants and retinal implants because hundreds of or thousands of electrodes may be needed to be connected to the necessary IC chips (see, K. D. Wise et al., *International Conference of the Engineering in Medicine and Biology Society on Neural Engineering* 2007, pp. 398-401). In comparison, a pacemaker has only one stimulating channel and a cochlear implant requires only 5 to 6 stimulating electrodes to be able to regain hearing capabilities of an impaired patient (see, K. Najafi et al., *IEEE Conference on Nano/Micro Enginnered and Molecular Systems,* 2004, pp. 76-97). In addition, in order to avoid possible infection and medical complications, it is desirable to have prosthetic devices completely inside a subject's body. This means that technologies for integration, connection and packaging of IC chips for high-lead-count implant devices are of high demand. As shown previously, aligned electrical connection can be done between parylene-C interfaces and high density multi-channel chips by a conductive epoxy squeegee technique (see, Jay H. C. Chang, Ray Huang, and Y. C. Tai, *Proc. TRANSDUCERS* 2011, pp. 378-381), where a PDMS mold was used to house the IC chips and serve as the safety squeegee buffer zone. However, it is too big to be implanted inside a human eyeball (<1~2 $cm^3$) (see, M. Humayun et al., *Vision Research,* 43 (2003), pp. 2573-2581). In addition, since the adhesion only relied on conductive epoxy contacting less than 2% of the total connection area, delamination could easily happen when even a small force was applied to the assembled devices. This would be especially serious during surgery. Since the next generation intraocular retinal prosthetics require the whole device, including coils, electrodes, stimulation chip and other ASICs to be fitted inside a human eyeball, the device must be further designed in terms of both size and surgical complexity.

Parylene-C has become a popular material for BioMEMS implant applications due to its superior properties (see, J. H. Chang et al, Proc. TRANSDUCERS 2011, pp. 390-393; J. H. Chang et al, *Proc. NEMS* 2011, pp. 1067-1070). It has also served as an intermediate layer for silicon wafer bonding (see, H. Noh et al, *J. Micromech. Microeng.* 14(2004), 625; H. Kim et al., *J. Microelectromech. Syst.* 14(2005), 1347-1355). However, the bonding between parylene-C and silicon is still problematic.

There are various processes for packaging integrated circuit (IC) dice. Some packaging techniques contemplate the creation of electronic modules that incorporate multiple electronic devices (e.g. integrated circuits, passive components such as inductors, capacitor, or resisters) into a single package. Despite the advances of the prior art, and although implantable devices have been developed with micro-electrical-mechanical system (MEMS) technology, there is a need for better packaging technology, especially for high-lead-count retinal and neural implants. The present invention provides these and other needs.

BRIEF SUMMARY OF THE INVENTION

The present invention provides substrates, methods and processes to assemble IC chips to thin-film substrates such as a parylene substrates for medical implants such as retinal implants. Advantageously, the inventive packaging technology can be used to produce 10,000 or more connections within an area as small as 36 $mm^2$, a chip size reasonable for retinal implants. The current invention provides methods for improving packaging techniques.

As such, in one embodiment, the present invention provides a method for fabricating a thin-film substrate such as a parylene substrate for attachment of a device, comprising:
  depositing a first thin-film layer such as a parylene layer on a silicon-wafer to form a bottom thin-film layer;
  depositing a metal to the bottom parylene layer to form an electrical connection;
  depositing a second thin-film layer such as parylene layer adjacent to the metal to form a top thin-film layer and a thin-film metal thin-film sandwich (e.g., parylene-metal-parylene sandwich);
  providing a mask adjacent to the top thin-film layer; and
  directing an etching beam onto the mask to fabricate the thin-film substrate (e.g., parylene substrate) for attachment of the device.

In another embodiment, the present invention provides the thin-film substrate (e.g., parylene substrate) made by the inventive process. The substrate is useful to integrate, connect and package IC chips for high-lead-count implant devices.

In order to validate this technology, chips designed with 268 connections to mimic real IC chips under development were used for the measurement of connection yield. In addition, after squeegee connection and encapsulation by a thick parylene-C coating, the connected chips underwent accelerated soaking tests in a high temperature saline solution. The results show that the technique provides exceptionally high connection yield.

In yet another embodiment, the present invention provides a method for assembling an integrated circuit to a thin-film substrate (e.g., parylene substrate), comprising:
  spin coating a photo-patternable adhesive or epoxy to an integrated circuit (IC) to form a covered IC;

masking the covered IC; and patterning the covered IC using photolithography to expose a plurality of bonding pads on the IC chip to form a patterned IC to integrate into the thin-film substrate (e.g., parylene substrate).

In still another embodiment, the present invention provides a biocompatible thin-film (e.g., parylene) substrate for attachment of a device, comprising:

a first thin-film (e.g., parylene) layer;

a metal adjacent to the first thin-film layer;

a second thin-film (e.g., parylene) layer adjacent to the metal to form a thin-film metal thin-film sandwich (e.g., parylene-metal-parylene sandwich), wherein the second layer of thin-film has an opening, the opening having at least one electrical contact provided on an internal surface thereof, the opening configured to accept at least one electrical circuit device and to provide electrical communication between the at least one electrical contact and the at least one electrical circuit device, the biocompatible thin-film (e.g., parylene) substrate configured to be implanted within a living organism after accepting the at least one electrical circuit device.

In certain aspects, the device having at least one electrical circuit is an integrated circuit (IC) chip. In addition, in one aspect the device such as an IC chip is integrated into the substrate by a conductive epoxy squeegee electrical connection. Preferably, the device is integrated into the substrate by a photo-patternable adhesive or photoresist used as a mechanical glue.

In another embodiment, the present invention provides:

a biocompatible package for low density connections, comprising:

a feedthrough layer;

an application specific integrated circuit (ASIC) face down on the feedthrough layer;

a printed circuit board (PCB) attached to the ASIC adapted for off-chip components and wire bonded to the feedthrough layer;

metal walls adjacent the feedthrough layer; and a metal lid to encase and make the biocompatible package.

These and other aspects, objects, and embodiments will become more apparent when read with the detailed description and figures which follow.

BRIEF DESCRIPTION OF THE DRAWINGS

FIG. 2B shows the backside of the discrete component area. FIG. 2C shows a close-up view of the chip integration; FIG. 2D shows a retinal tack; FIG. 2E shows a schematic of an eye and integration of a fabricated flexible parylene-C substrate connected with a chip.

FIGS. 4B-4C show pads also served as alignment marks.

FIG. 5B shows AZ4620 baked at 140° C. for 30 minutes in a vacuum oven; FIG. 5C and FIG. 5D show the slope formed by reflow is beneficial for conductive epoxy to be fed through.

FIGS. 6A-6B show the gluing area was about 2% as is shown in FIG. 6A; FIG. 6B shows the gluing area increased to about 94% (2%+92%) by the extra photoresist used as glue.

FIG. 8B shows the adhesive interface after parylene peeling.

FIG. 9B shows a real testing sample after bonding; FIG. 9C shows the schematic representation of the testing sample.

FIG. 12B shows the peeling force vs bonding time for different photo-patternable adhesives.

FIGS. 13A-13C show in FIG. 13A a surgical parylene-C device connected with silicon chip and discrete components; FIG. 13B and FIG. 13C show metal pads are exposed with other area covered by adhesives.

FIG. 16B shows the connection between a parylene substrate and dummy chip; FIG. 16C shows the yield vs separation of pads; FIG. 16D shows the yield vs side length of pads.

DETAILED DESCRIPTION OF THE INVENTION

I. Embodiments

The present invention relates to biomedical implants in general and in particular to biomedical implants that employ a thin-film (e.g., parylene) substrate that allows the total connection and fabrication of a biomedical implant comprising semiconductor chips and/or other pre-manufactured electrical components. In one embodiment, the present invention provides a method for fabricating a thin-film substrate such as a parylene substrate for attachment of a device, comprising:

depositing a first thin-film layer such as a first parylene layer on a silicon-wafer to form a bottom thin-film layer;

depositing a metal to the bottom thin-film (e.g., parylene) layer to form an electrical connection;

depositing a second thin-film layer such as second parylene layer adjacent to the metal to form a top thin-film layer and a thin-film metal thin-film sandwich (e.g., parylene-metal-parylene sandwich);

providing a mask adjacent to the top thin-film layer; and directing an etching beam onto the mask to fabricate the thin-film substrate (e.g., parylene substrate) for attachment of the device. The first thin-film layer can be the same or different than the second thin-film layer. Although parylene is the preferred substrate, a skilled artisan will appreciate that the material can be other thin-film polymers such as polyimide, Teflon, kapton, or a printed circuit board (PCB) and the like. The remainder of the application will use parylene as an illustrated example. Other thin-films can also be used.

Figure 1A:
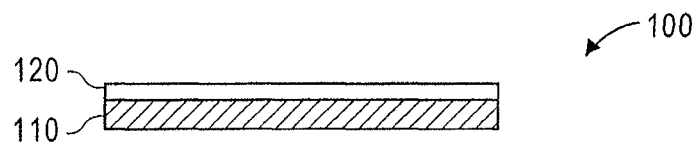
FIGS. 1A-1K show a fabrication process of a flexible parylene-C connection substrate and chip integration according to one embodiment of the present invention.

In certain aspects, the present invention provides a fabrication process 100 for a parylene-substrate, such as a flexible parylene-C substrate. In one exemplary embodiment, FIG. 1A shows a 5 µm first parylene-C layer (bottom layer) 120 deposited on a silicon substrate 110 such as a HMDS treated silicon wafer, which aids in the device being detached such as being released in distilled or deionized water, preferably deionized water.

Figure 1B:
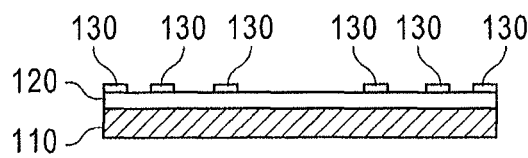
Figure 1C:
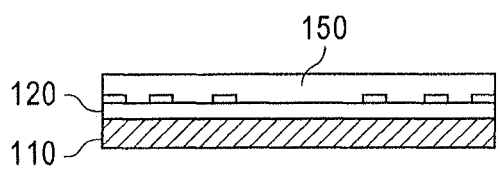
Figure 1D:
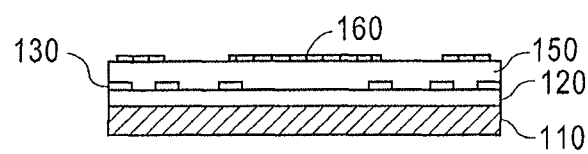
Figure 1E:
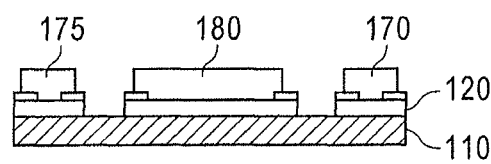
Figure 1F:
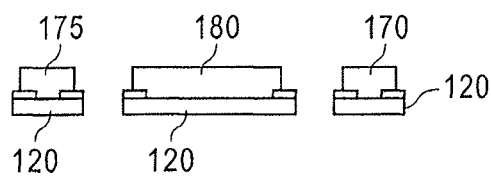

Next, as is shown in FIG. 1B, adjacent to the first parylene layer 120 (bottom parylene layer) is a metal 130 such as a titanium/gold (Ti/Au) alloy for a metal lift-off. The metal provides an electrical connection. A second parylene layer 150 (top layer) such as a thicker parylene-C (about 40 µm) layer is then deposited to complete the parylene-metal-parylene sandwich structure as is shown in FIG. 1C. The process includes providing a mask 160 such as a metal mask (e.g., aluminum) deposited as a parylene-C etching mask to etch through the thick parylene-C layer as is shown in FIG. 1D. Finally, electrode sites 170, 175 and device contour 180 are defined by reactive ion etching (such as a 2-step $O_2$ plasma etching as is shown in FIG. 1E) or deep reactive ion etching (DRIE) can be used. FIG. 1F shows the flex being released from the wafer 110.

Although the foregoing example uses parylene-C, the processes and embodiments of the device herein are not so limited. Other parylenes such as parylene N, C, D, HT, AM, A or combinations thereof can also be used. Parylene-C is the preferred parylene. Although parylene is the preferred substrate, a skilled artisan will appreciate that the material can be other thin-film polymers such as polyimide, Teflon, Kapton, or a printed circuit board (PCB) and the like.

Other materials useful for substrate and/or carrier design include, but are not limited to, silicon, glass, steel, G10-FR4, or any other FR4 family epoxy, etc. In some embodiments, the silicon substrate is used only as a carrier during fabrication and is accordingly removed before the package is complete. In other embodiments, the carrier remains an integral part of the package.

In certain aspects, the silicon-wafer used in the methods is treated with 1,1,1,3,3,3-hexamethyldisilazane (HMDS). A skilled artisan will appreciate other treatments can be used to release the parylene structure from the silicon wafer.

In certain aspects, the first parylene layer 120 and the second parylene layer 150 are deposited on the silicon substrate by chemical vapor deposition (CVD). The first layer has a thickness of between about 0.1 µm to about 100 µm thick such as 10, 20, 30, 40, 50, 60, 70, 80, 90, or 100 µm. Preferably, the thickness of the first parylene layer (bottom layer) is between about 1 µm and about 10 µm thick such as about 1, 2, 3, 4, 5, 6, 7, 8, 9, or 10 µm thick.

Typically the second parylene layer (top layer) 150 is thicker than the first parylene layer 120. In one instance, the second parylene layer is between 10 µm and 200 µm thick such as 10, 20, 30, 40, 50, 60, 70, 80, 90, 100, 110, 120, 130, 140, 150, 160, 170, 180, 190 or 200 or even thicker. Preferably, the second parylene layer is between 20 µm and 60 µm thick such as about 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 µm thick.

In certain aspects, the metal 130 used for the lift-off is a titanium/gold (Ti/Au) alloy. However, other suitable metals and alloys include, but are not limited to, Cr/Au, Ni/Au, Ti/Au, Al/Ti, Ag/Ti, Cr/Au/Ti/Ni/Au, Ni/Pd/Au, Ti/Ni/Au or combinations thereof. Those of skill in the art will know of other metals useful for the present invention.

The process includes providing a mask such as a metal mask deposited as a parylene-C etching mask to etch through the second parylene-C layer. In general, etching is a reactive ion etching (RIE) masked by a metal mask. In addition, deep reactive etching can be used (DRIE). Other suitable mask materials are also useful. The RIE can be oxygen plasma etching.

A skilled artisan will appreciate that the parylene layers of the parylene devices described herein are not limited to two parylene layers. In addition, the metal of the parylene device is not limited to a single metal. The parylene devices are based on a sandwich structure. As long as a metal is sandwiched by a top and a bottom parylene layer, there can be numerous layers stacked on the substrate. In addition, there can be a plurality of masks to open the electrodes and define the contour of the device(s).

In certain instances, the process described is used to generate multiple parylene-metal-parylene sandwich layers on a carrier (e.g., a silicon wafer) such as a plurality of sandwich layers including 2, 3, 4, 5, 6, 7, 8, 9, 10 or more parylene-metal-parylene sandwich layers. Although the process just described generates 1 sandwich layer, a skilled artisan will appreciate that the process can be repeated to make any number of sandwich layers.

In still other aspects, the invention includes a parylene substrate made by the processes herein. As is described in more detail below, the invention provides attaching a device to the parylene substrate such device includes, for example, an integrated circuit and other discrete components.

Figure 1G:
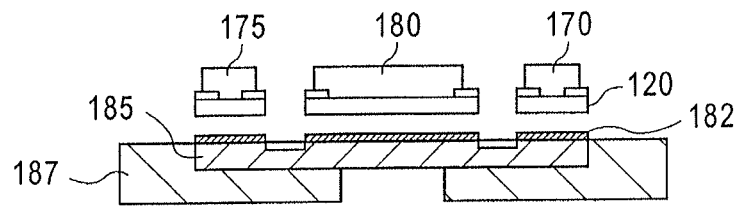
Figure 1H:
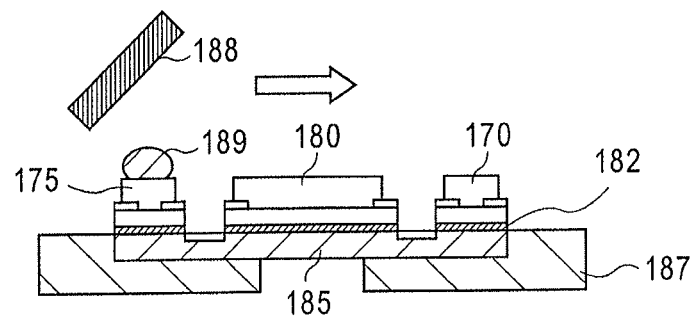
Figure 1I:
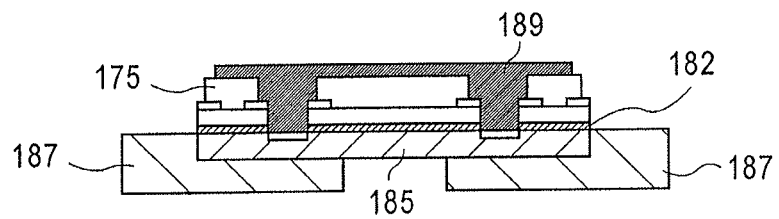
Figure 1J:
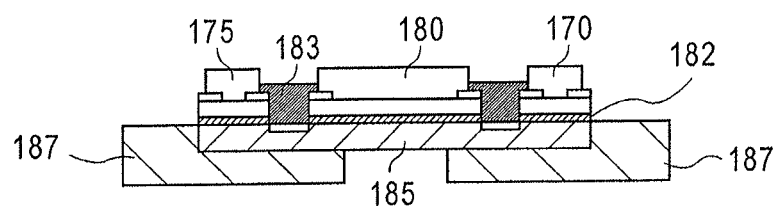
Figure 1K:
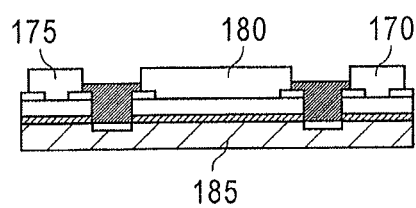

In one aspect, after the flex is released, an ASIC is integrated with the released flex. For example, FIG. 1G shows the flex previously released from the wafer being aligned with the ASIC 185 with a photo-patternable adhesive 182 placed in a mold 187. In FIG. 1H, the flex is bonded with ASIC 185 with PPA 182 and ready for conductive epoxy 189 using a squeegee 188 process. As is shown in FIG. 1I, after a conductive epoxy squeegee process, some conductive epoxy residue 189 is left on the top surface, which may cause a shortage. As is shown in FIG. 1J, the top is cleaned to provide a cleaned top surface to avoid shortage. In FIG. 1J, the conductive epoxy 183 is kept inside cavities to make a connection between the flex and ASIC. FIG. 1K shows the release of the assembly device from the mold.

In certain aspects, the inventive thin-film (e.g., parylene) substrate hosts electronic components such as application specific integrated circuits (ASICs), which are interconnected via metallization traces, such as about 3.7 µm wide metallization trace. In one embodiment, the fabricated flexible parylene-C substrate is connected with an IC chip and other discrete components. In certain other aspects, the substrate or micro-module of the present invention contains a variety of components including, but not limited to, one or more integrated circuits, ASICs, interconnect layers, heat sinks, conductive vias, passive devices, MEMS devices, sensors, pre-manufactured electrical components, transistors, resistors, capacitors, inductors, micropumps and filters. The components are arranged and stacked within the module in a wide variety of different ways. The layers and components of the module can be deposited and processed using various conventional wafer level processing techniques, such as spin coating, lithography and/or electroplating.

The parylene package can include many other types of devices and components than the ones illustrated. The package can also contain almost any number of active and/or passive devices. Examples of such active and/or passive devices includes resistors, capacitors, oscillators, magnetic cores, MEMS devices, sensors, cells, communication devices, integrated thin film battery structures, inductors, and the like. These devices can be positioned and/or stacked in various locations within the package. The components may take the form of prefabricated discrete components or may be formed in-situ. One advantage of the lithography-based process used to create the present package is that these and other components can be formed in-situ during the layered formation of the package. That is, while prefabricated, discrete components can be placed in almost any position within package, components can also be fabricated directly onto any photo-imageable layer using any suitable technique, such as conventional sputtering and/or electroplating.

Figure 2A:
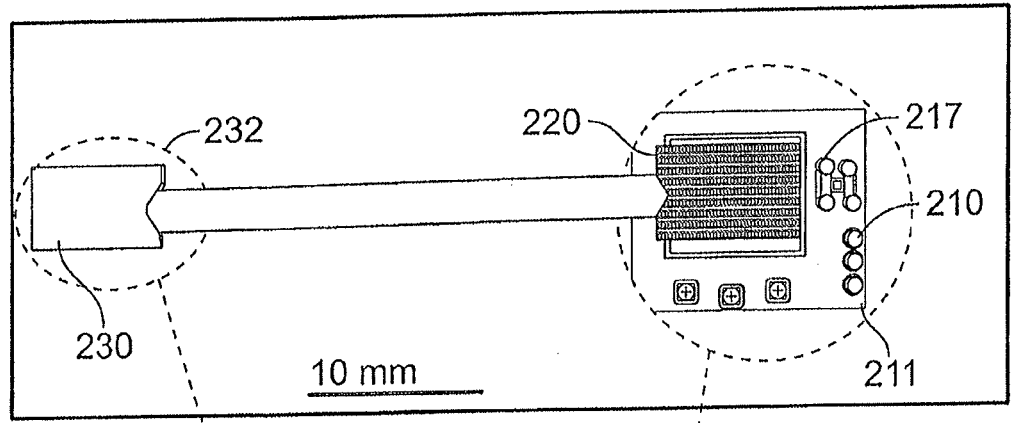
FIGS. 2A-2E show in FIG. 2A a schematic representation of the fabricated flexible parylene-C substrate connected with a chip and discrete component.
Figure 2B:
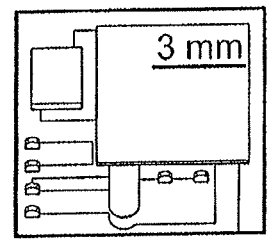
Figure 2C:
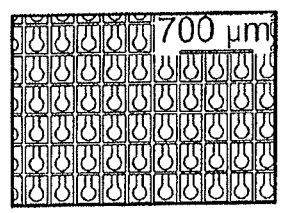
Figure 2D:
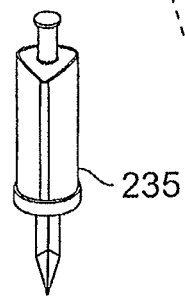
Figure 2E:
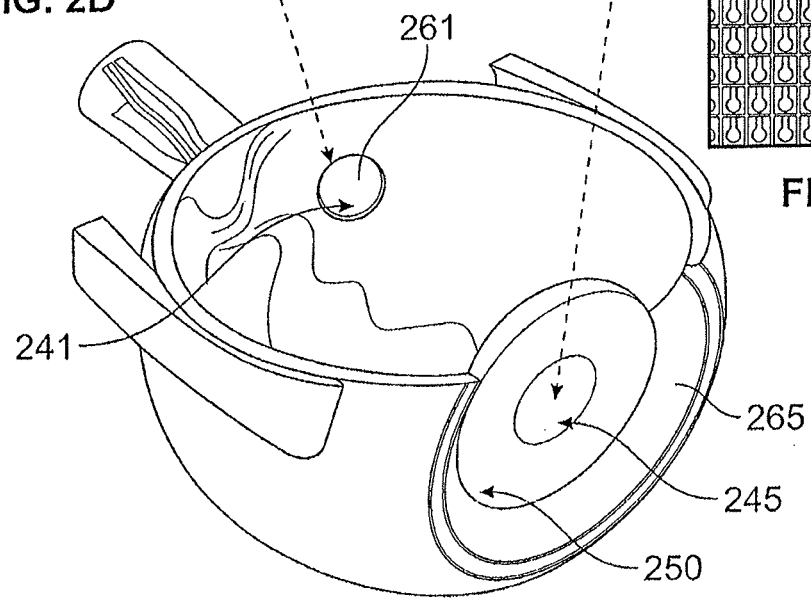

Turning now to FIG. 2A, a schematic representation 200 is shown of the fabricated flexible parylene-C substrate 210 connected with an integrated chip 220 and discrete components e.g., capacitor 211 and oscillator 217. In certain aspects, the multi-electrode array 230 with outputs 232 is placed on the macula of a human eye or an eye of another mammal and can be fixed by a retinal tack 235 (FIG. 2D). In one instance, integrated discrete components are placed on or in an eyeball. FIG. 2B is the backside of the discrete component area. FIG. 2C shows a close-up view of the chip integration. FIG. 2E is a schematic of an eye showing positioning of an electrode array 241, integrated ASICs 245 and an intraocular RF coil 250.

As shown in FIG. 2A, the discrete components such as for example a capacitor 211 and an oscillator 217 are mounted and connected by conductive epoxy to make an electrical connection. In certain instances, two incisions or suture holes are made for the device to be fixed in an eyeball 261, 265 (see, FIG. 2E). In one aspect, a multi-electrode array 230 is placed on the macula and fixed by a retinal tack 235. FIG. 2E also shows the electrode array 241, inside one incision 261 and the integration of the application specific integrated circuit 245 in the other incision 265. An intraocular RF coil 250 is also shown. The interconnection part is preferably about 0.1 mm to about 6 mm wide such as about 0.1, 0.2, 0.3, 0.4, 0.5, 0.6, 0.7, 0.8, 0.9, 1, 2, 3, 4, 5, or 6 mm wide. In certain instances, the interconnection is about 2 mm wide. In certain instances, the interconnection depends on the incision size for surgery on the eyeball. However, in most instances, the width is about 2 or 3 mm.

In certain instances, IC chips having high-density and multi-channel bonding pads (e.g., pad size smaller than about 100 μm×100 μm; pitch smaller than about 200 μm) can be connected with a parylene substrate by a conductive epoxy squeegee technique. Other discrete components with larger bonding pads, such as caps and oscillators, can be connected with a parylene substrate manually by conductive epoxy using needles. Power and data coils with larger bonding pads can also be connected with a parylene substrate manually by conductive epoxy using needles. The whole integrated device is then fixed inside an eyeball by a retinal tack (e.g., close to electrode array).

Figures 3A, 3B:
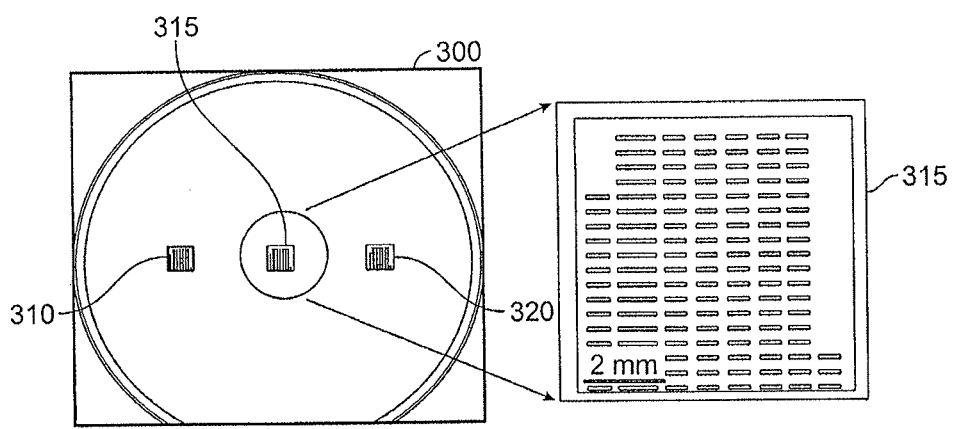
FIGS. 3A-3B show a custom holder for chip assembly technique.

In another embodiment, the present invention provides methods for integrating the flexible parylene substrate with an IC chip and other discrete components. The method includes chip pattern lithography, including photoresist spinning, baking, exposing, and developing as well as integrating the IC chip into the flexible parylene substrate. As shown in FIG. 3A, IC chip assembly can be done in a custom holder 300.

In operation, chips 310, 315, 320 are first secured in a holder 300, and all the chip pattern lithography, including photoresist spinning, baking, exposing, and developing is done in this holder in series. After chip integration with a parylene-C interface by a conductive epoxy squeegee connection, the chip 315 can be released from the back side of the mold, which is beneficial for the whole device to be implanted inside the eyeball. The chip can be integrated and packaged into the flexible parylene substrate. The processing of the IC chips to form a patterned IC chip is typically done on a custom chip pattern mold. FIG. 3A also shows the mold can serve as a safety buffer zone for a squeegee process. The size and the depth of the mold is designed to accommodate various sizes of the chip. FIG. 3B shows an expanded view of an IC chip.

In one example of a squeegee process of the present invention, a commercially available conductive epoxy is first mixed well and applied on the surface of an edge of the parylene substrate. In certain instances, the parylene substrate has pre-designed holes and/or wells that are etched during the fabrication process. The holes and/or wells serve as a screen for this process after the IC chip is aligned and bonded well with the parylene substrate. A rubber squeegee is then used to push the epoxy across the surface, so the epoxy fills the holes and/or wells in the parylene substrate, to electrically connect the parylene substrate and IC chip.

Figure 4A:
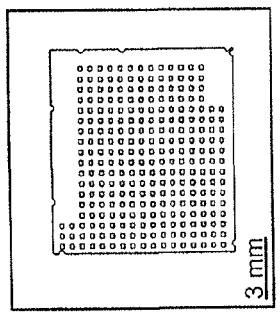
FIGS. 4A-4C show in FIG. 4A a dummy chip for assembly yield test.
Figure 4B:
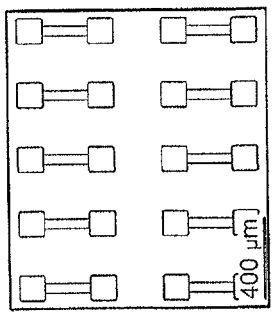
Figure 4C:
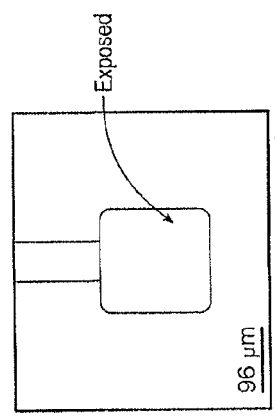

In certain instances, dummy chips with conductive traces are fabricated to simulate the actual chip and special pads are pre-connected for connection yield measurement. For example, FIG. 4A shows a dummy chip for an assembly yield test. FIG. 4B shows pads can also serve as alignment marks. FIG. 4C shows a metal pad exposed with a resolution of around 5 μm being achieved.

The present invention provides methods and processes for a low-temperature bonding between a thin-film (e.g., parylene such as parylene C) and silicon using photo-patternable adhesives. This method can be used to determine the bonding pads and also reduce the residual stress in packaging. Advantageously, this low-temperature bonding allows selectively local area bonding, without applying a high electric field. Thus it is especially suitable for the integration of a parylene substrate with microelectronics in MEMS packaging.

As such, in yet another embodiment, the present invention provides a method for assembling an integrated circuit to a thin-film substrate. Although parylene is the preferred substrate, a skilled artisan will appreciate that the material can be other thin-film polymers such as polyimide, Teflon, kapton, or a printed circuit board (PCB) and the like. The method comprises:
  spin coating a photo-patternable adhesive or epoxy to an integrated circuit (IC) to form a covered IC;
  masking the covered IC; and
  patterning the covered IC using photolithography to expose a plurality of bonding pads on the IC to form a patterned IC, for integration into a thin-film (e.g., parylene) substrate.

In certain instances, the invention provides low-temperature bonding processes to facilitate the connection and packaging of various components for use as biomedical implants. In certain instances, the bonding technology can be used to facilitate the connection between parylene-C substrates and an IC as well as descrete components, which substrates have pre-metalized electrical connections. The chips are preferably bound on the substrates with proper alignment so the metal pads on the parylene substrates and the metal pads on the chips line up.

In certain instances, commercially available photo-patternable materials such as photo-patternable adhesive or epoxy can be used. In certain aspects, the photo-patternable material is a photoresist. Suitable photoresist includes SU-8, AZ4620, AZ1518, AZ4400, AZ9260, THB-126N, WPR-5100, BCB, polyimide and the like. The processing conditions are facile with respect to bonding temperature, pressure, time, and surface treatment. The results show that for example, the epoxy-based SU-8 is very effective with a peeling force up to 6.3N.

Figure 5A:
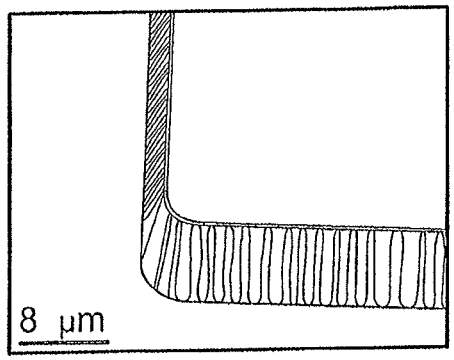
FIGS. 5A-5D show in FIG. 5A unbaked AZ4620.
Figure 5B:
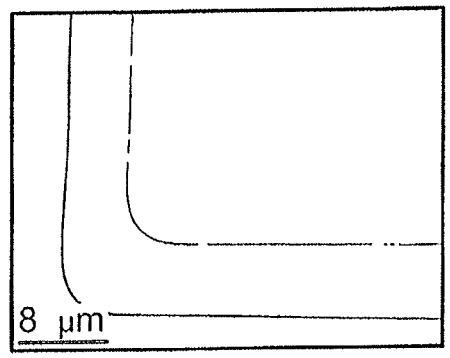
Figure 5C:
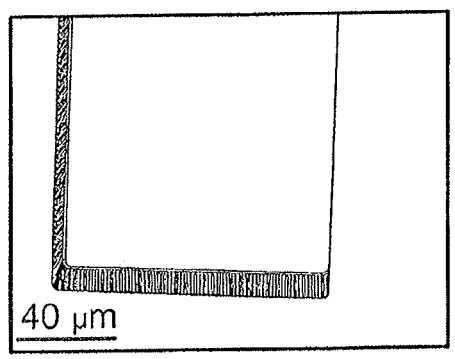
Figure 5D:
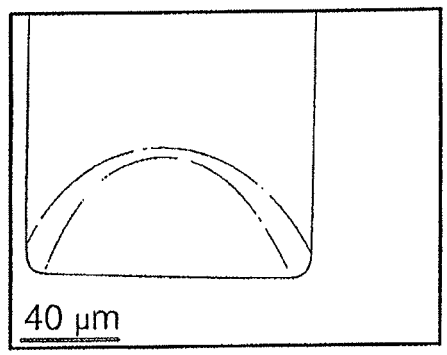

In certain instances, AZ4620 photoresist is used in the processes due to excellent reflow properties (P. J. Chen et al., *J. Microelectromech. Syst*, 17 (2008), pp. 1352-1361). The patterned AZ4620 photoresist is baked at 100° C. to about 180° C. such as 140° C. for 10 minutes to 80 minutes such as about 30 minutes in vacuum oven and its smooth surface formed by reflow helps the conductive epoxy refill, as shown in FIG. 5 A-D. The side lengths were almost the same before and after baking such that the reflown photoresist does affect conductivity by covering the whole metal pad. In one specific embodiment, in no way limiting, FIG. 5A illustrates unbaked AZ4620. FIG. 5B shows AZ4620 baked at 140° C. for 30 minutes in a vacuum oven. FIGS. 5C and 5D show that the slope formed by reflow is beneficial for conductive epoxy to be fed through. Advantageously, the side lengths show no change before and after baking.

In previous applications, conductive epoxy was fed through the cavity embedded in a parylene-C substrate and relied on to make both electrical and mechanical connections. As shown in FIG. 6A, the prior art process uses only conductive epoxy 615 to connect the parylene substrate and the chip 602. The metal pad is shown as 625. In the process of the present invention, both conductive epoxy 615 and photo-patternable adhesive (e.g., photoresist) 610 such as AZ4620 is used. In fact, after applying AZ4620 (as glue here) to the chip 602, the total gluing area between parylene-C substrate and a chip 602 is increased from 2% to 94%, as shown in FIG. 6B. In certain instances, the unnecessary pads were also covered to avoid shortage happening underneath the parylene-C interface during a squeegee connection process.

The high-density connections between the chip and the parylene-C substrate were again done by conductive epoxy squeegee, while the custom holder provided the safety buffer zone for squeegee to totally replace the function of PDMS holders (see, Jay H. C. Chang, Ray Huang, and Y. C. Tai, *Proc. NEMS* 2011, pp. 1110-1113).

II. Low-Temperature Bonding Between Parylene-C and Silicon

In certain instances, the photo-patternable adhesives are first spin-coated on clean silicon wafers with for example, HMDS and oxygen plasma treatments, followed by standard photolithography process to define the bonding pads. In certain preferred aspects, the methods include baking the patterned IC to form a smooth surface. In certain other instances, the parylene substrate is first treated with oxygen plasma to enhance bonding with photo-patternable adhesives. In still other instances, the IC chip is treated by HMDS and/or oxygen plasma to enhance bonding with photo-patternable adhesives.

Focusing on the application on chip integration, as an illustrative example of photo-patternable adhesives, SU-8 (13 μm and 28 μm), and AZ4620 (10 μm and 19 μm) are selected as an illustration to create suitable aspect ratios of the cavity or opening. Other photoresists include AZ1518, AZ4400, AZ9260, THB-126N, WPR-5100, BCB, polyimide and the like.

Figure 7:
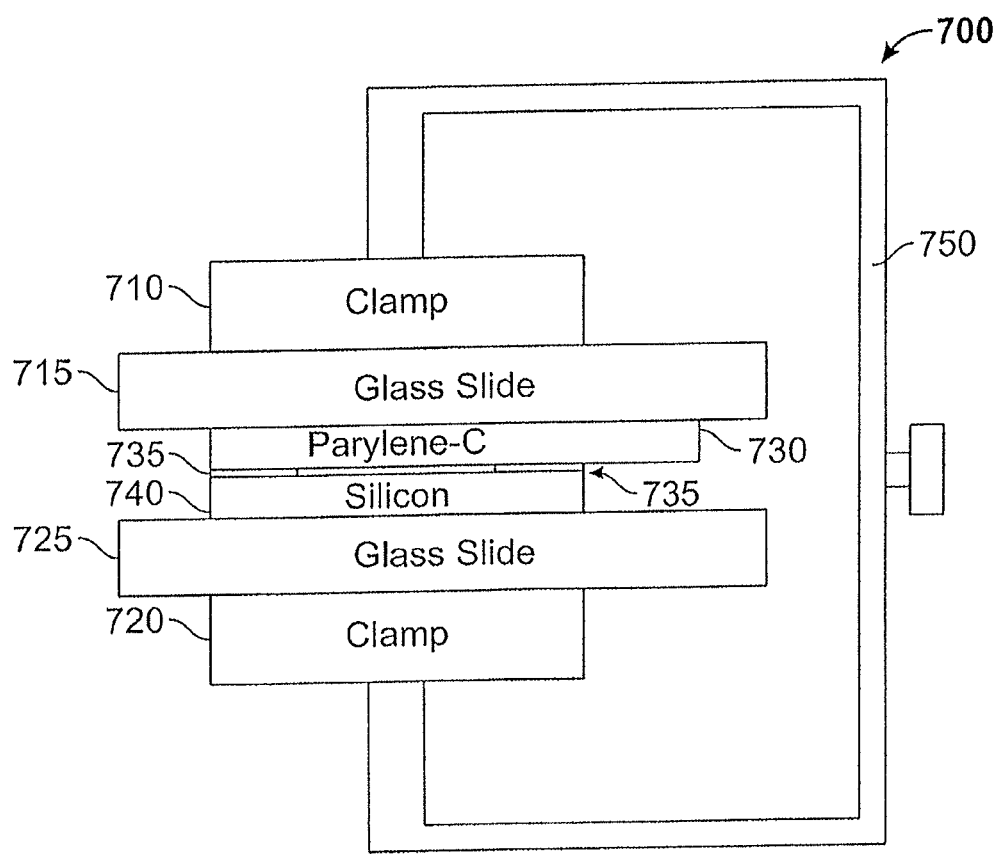
FIG. 7 shows a schematic representation of a clamp as the bonding tool on the testing samples.

As is shown in FIG. 7, a clean 30 μm parylene-C film 730 treated by oxygen plasma is then aligned with a diced wafer 740 and the structure is sandwiched by two glass slides 715, 725. A clamp 750 having two arms 710, 720 is used as a bonding tool to make good contact and apply constant force on the testing samples. The heating process is operated in a vacuum oven and the maximum testing temperature is set to be about 120-180° C. such as about 150° C. to prevent damage to the IC chips.

Figure 8A:
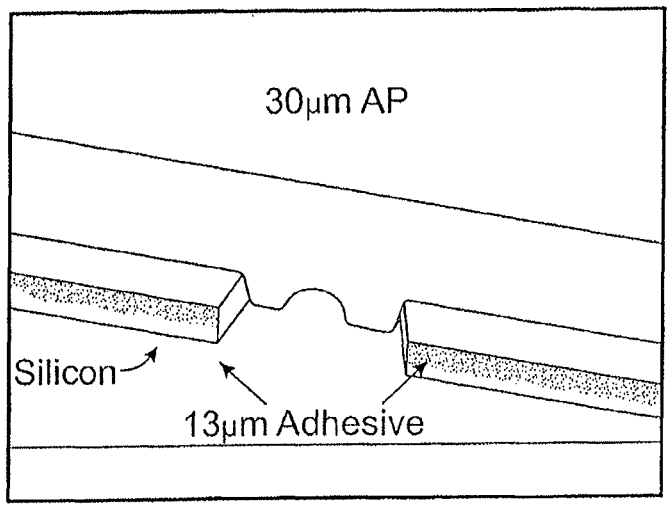
FIGS. 8A-8B show in FIG. 8A a cross-sectional SEM image of the bonding (2 MPa, 130° C.)
Figure 8B:
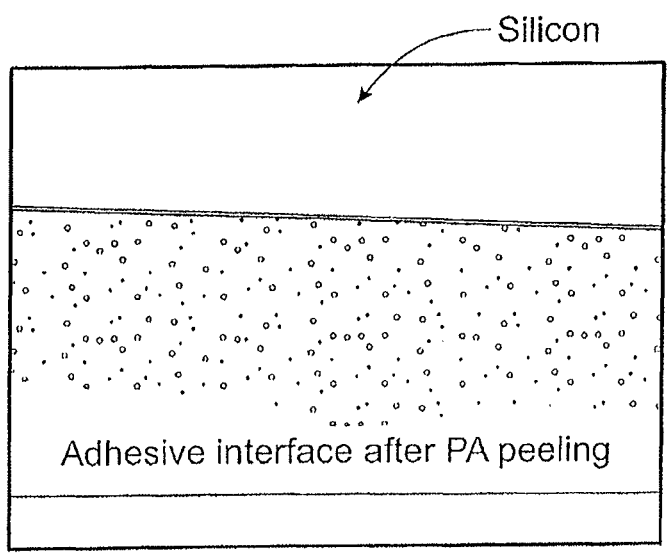

FIGS. 8A and 8B show one example of cross-sectional SEM images of samples bonded by photo-patternable adhesives. The bonding pads are well defined with desired thickness and the shape of the microstructures is not changed during the bonding process. Moreover, the flexible intermediate adhesives does not cause residual stress after bonding.

In one aspect, the methods include first treating the parylene substrate with oxygen plasma treatment to enhancing bonding. Such plasma treatment conditions include, for example, about 10 W to about 100 W such as about 50 W; 100 mtorr to about 300 mtorr such as about 200 mtorr; and 0.1 minute to about 5 minutes such as about 1 minute duration.

In certain instances, each of the plurality of bonding pads is between 1 μm and 10 μm. In certain instances, the bonding pads can each be different dimensions. The thickness of photo-patternable adhesives on the IC chip is from 10 μm to 30 μm such as 10, 11, 12, 13, 14, 15, 16, 17, 18, 19, 20, 21, 22, 23, 24, 25, 26, 27, 28, 29 or 30 μm. In certain instances, the patterned IC and a parylene substrate are assembled using conductive epoxy or paste. The methods include delivering conductive epoxy to make a high-density multi-channel IC chip connection by a high-throughput squeegee technique. In certain instances, the high-density multi-channel IC chip is greater than 1000 channels on a 25 mm$^2$ chip area or even 10,000 channels on a 36 mm$^2$ or about 5-300 channels per mm$^2$ chip area.

In certain aspects, when IC chips have a pitch size larger than about 200 μm, applying conductive epoxy is performed with needles having a diameter smaller than 100 μm. As discussed above, the process on IC chips to form a patterned IC chip is done on a custom chip pattern mold. The mold serves as a safety buffer zone for the squeegee process. The size and the depth of the mold are designed to accommodate the size of the chip.

Figure 9A:
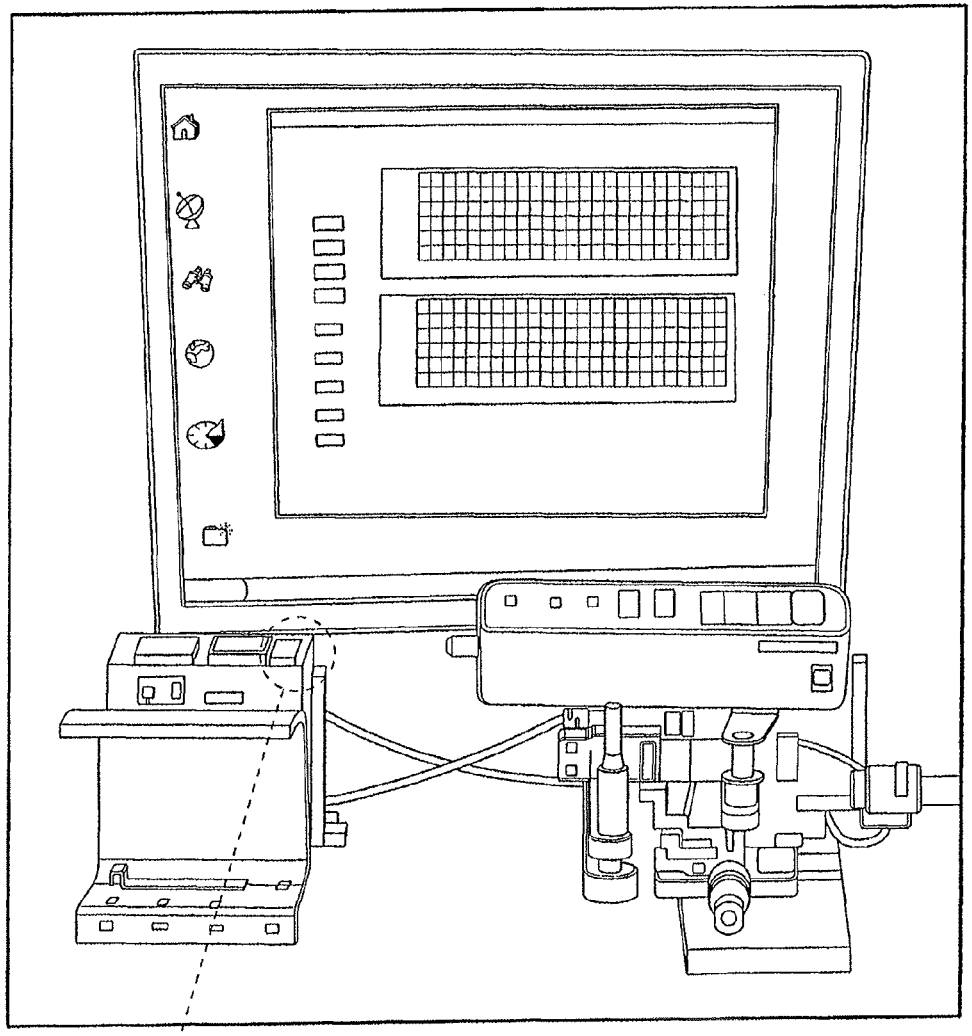
FIGS. 9A-9C show in FIG. 9A the setup of the force gauge to measure the peeling force.
Figure 9B:
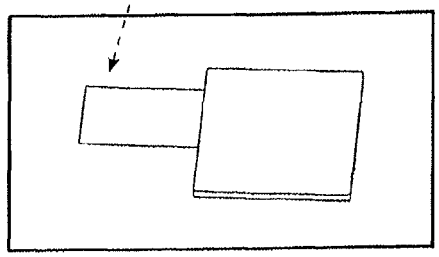
Figure 9C:
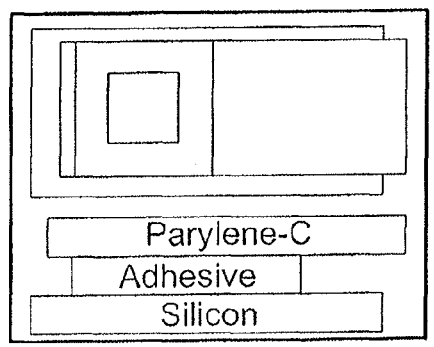

As is shown in FIG. 9A, the peeling force is measured by a force gauge setup to investigate bonding strength. FIG. 9B shows a testing sample after bonding; FIG. 9C shows a schematic representation of the testing sample.

Figure 10:
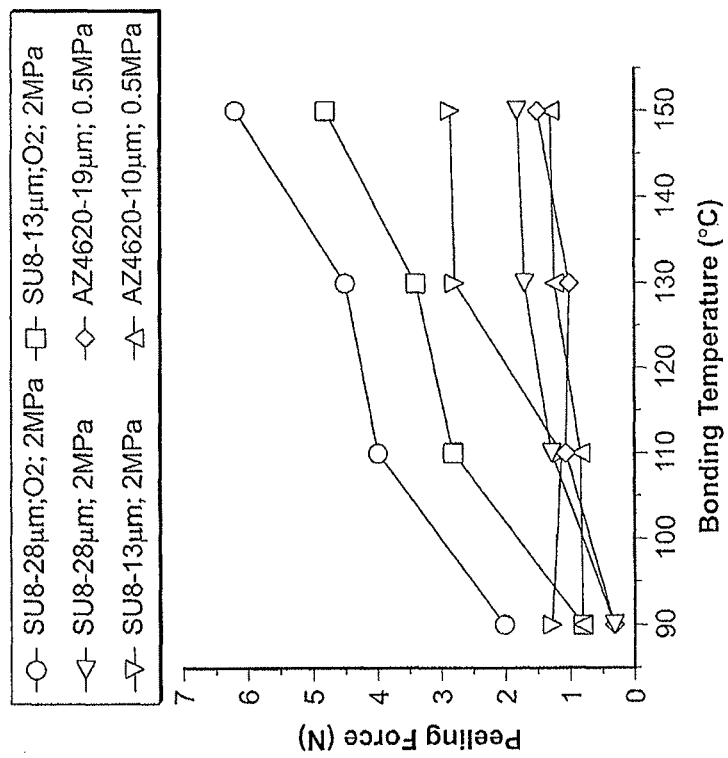
FIG. 10 shows the peeling force vs bonding temperature for various photo-patternable adhesives.

Each data point represents the average of five measurements. Force gauge is fixed on a motorized stage to pull the partially peeled film at 90 degree with a speed of 100 μm/s. Peeling force as a function of bonding temperature is shown in FIG. 10.

Figure 11:
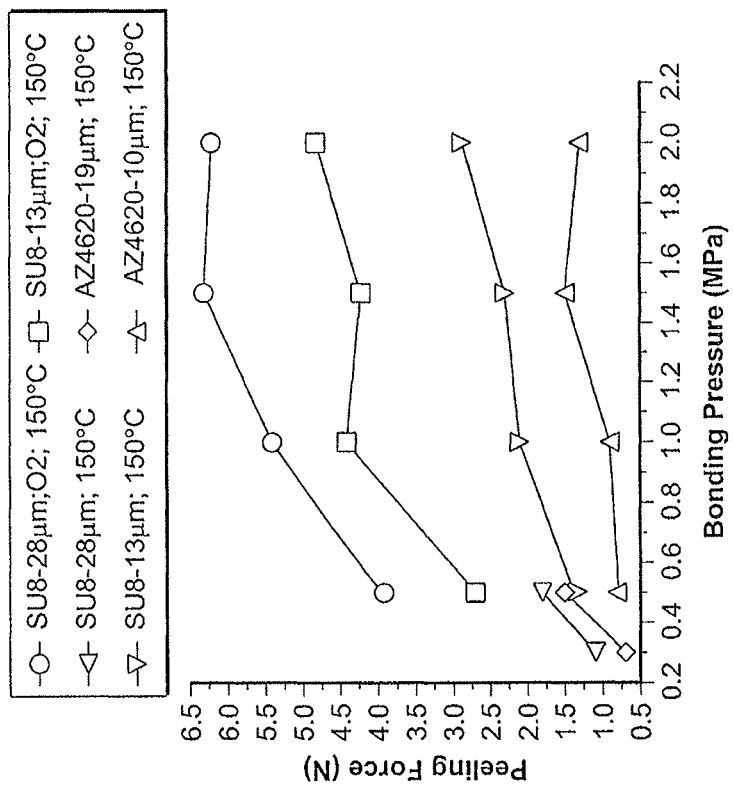
FIG. 11 shows the peeling force vs bonding pressure for various photo-patternable adhesives.

FIG. 11 shows peeling force as a function of bonding pressure. After analaysis, the results show that the higher the bonding temperature and pressure, the stronger the bonding.

Figure 12A:
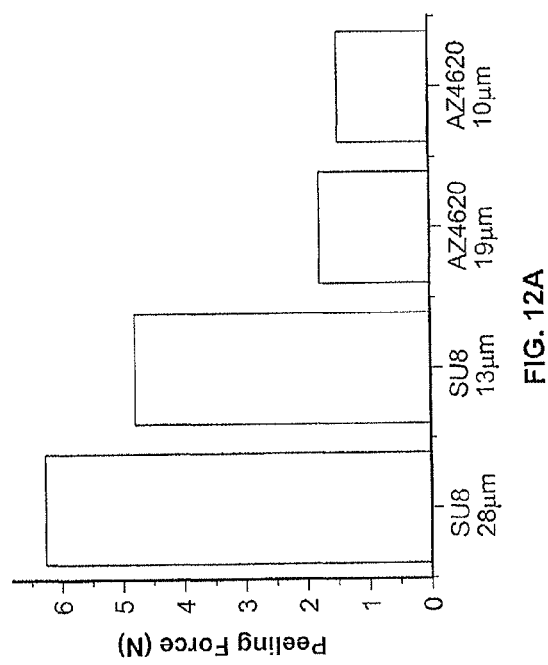
FIGS. 12A-12B shows in FIG. 12A the maximum peeling forces of different photo-patternable adhesives.
Figure 12B:
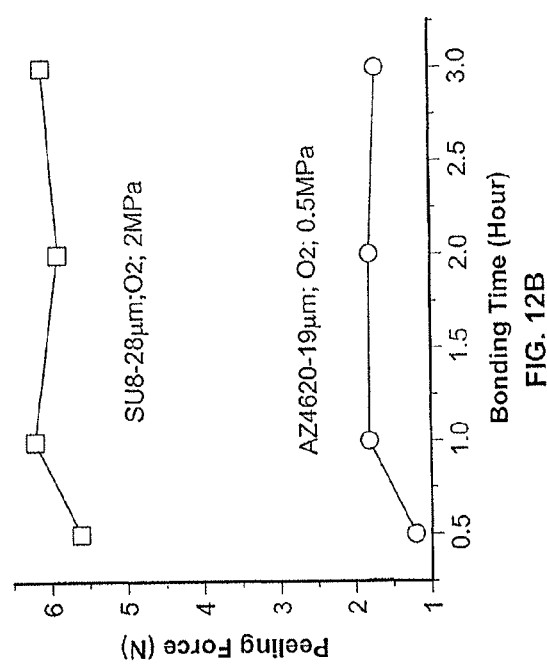

Advantageoulsy, parylene-C film treated by oxygen plasma dramatically enhances the bonding for photo-patternable adhesive such as photoresists (e.g., SU-8) (see, Blanco F J et al., *J. Micromech. Microeng.* 14 (2004), 1047-1056). SU-8 microstructure will not deform even under bonding pressure of 2 MPa where the maximum bonding forms. FIG. 12A shows the maximum peeling force of different photopatternable adhesives. FIG. 12B shows the peeling forece versus bonding time for different photo-patternable adhesives. Z4620 can withstand pressure up to 0.5 MPa. In certain aspects, the bonding time has almost no effect on the bonding strength when the samples are heated more than one hour.

As a demonstration, this technique is applied on a 268-channel conduction chip integrated with parylene-C surgical device for retinal implant (FIG. 13). After patterning the adhesives on chips (see, J. H. Chang et al, *Proc. MEMS* 2012, pp. 353-356), the spatial resolution of bonding pads built by SU-8 can be 5 μm. The bonding area is increased from 2% to 94% and the measured connection yield is improved from 92% to 98%.

This low-cost and low-temperature bonding process is proven to enable the sealing of MEMS structures.

In another embodiment, the present invention provides a biocompatible thin-film substrate. Although parylene is the preferred substrate, a skilled artisan will appreciate that the material can be other thin-film polymers such as polyimide, Teflon, kapton, or a printed circuit board (PCB) and the like. The invention provides a thin-film (e.g., parylene) substrate for attachment of a device, comprising:

a first thin-film (e.g., parylene) layer;
a metal adjacent to the first thin-film (e.g., parylene) layer;
a second thin-film (e.g., parylene) layer adjacent to the metal to form a thin-film metal thin-film (e.g., parylene-metal-parylene) sandwich, wherein the second layer of parylene has an opening or cavity, the opening having at least one electrical contact provided on an internal surface thereof, the opening configured to accept at least one electrical circuit device and to provide electrical communication between the at least one electrical contact and the at least one electrical circuit device, said biocompatible thin-film (e.g., parylene) substrate configured to be implanted within a living organism after accepting the at least one electrical circuit device.

In certain aspects, the device having at least one electrical circuit is an integrated circuit (IC) chip. In addition, the device such as an IC chip is integrated in the substrate by a conductive epoxy squeegee electrical connection. Preferrably, the device is integrated into the substrate by a photo-patternable adhesive used as a mechanical glue. In one embodiment, the whole structure (e.g., the device having at least one electrical circuit is an integrated circuit (IC) chip) is conformally coated and sealed with parylene-C (poly-para-xylylene-C), and if necessary, with medical grade epoxy to achieve total encapsulation for biocompatibility.

In certain instances, once the device is implanted, there can be communication with the implanted device and an external device. Communication can be performed using either percutaneous connectors or wireless communication methods. Some of the kinds of signals that are communicated between the implanted device and an external device include power signals and data signals. Power signals can include signals that provide power from an external power supply to an implanted device, so that a battery present in the implanted device can be maintained in a suitable state of charge, or so that a battery can be eliminated from the implanted device. For some conventional devices having batteries, surgery may become necessary to replace the device because its battery is expected to reach the end of its useful life. Any surgery poses a health risk and unnecessary surgery is best avoided if possible, especially in persons who already have health issues. Accordingly, implantable devices that do not have to be replaced because of a battery are advantageous.

Data signals can include data signals from an external detector to an implanted device (such as providing an electrical signal corresponding to an audible signal received by a microphone to a cochlear implant for communication by way of a person's nervous system to the person's brain), control signals from an external detector to an implanted device that provide the ability to control the implanted device by using such signals (e.g., controlling the state of operation of the implanted device to meet the needs of the person), and data signals from the implanted device to an external device to monitor the condition and operation of the implanted device itself, to monitor the condition of the person (such as pulse rate, cardiac signals, or other signals relating to the condition being treated) and conditions in the vicinity of the implanted device (such as physiological signals, e.g., temperature, pressure, pH), or to monitor the signals the implanted device is applying to the person. In some embodiments, data signals can be used to "tune" or "reprogram" the implanted device to take advantage of improvements in understanding of the person's condition and the intervention, assistance, or treatment that the person should have, or provide improvements in the implantable device operation and control procedures or operational software that are developed after the device is implanted.

Additional integrated circuits within package or module can be arranged in a wide variety of ways and may be placed at other location within the package. By way of example, different integrated circuits may be positioned in different photo-imageable layers and/or within the same layer. In various embodiments, the integrated circuits can be stacked, positioned side-by-side, placed in close proximity to one another and/or be separated by a substantial distance relative to the overall size of package. Integrated circuits can also have a variety of different form factors, architectures and configurations. For example, they may take the form of relatively bare dice (e.g., unpackaged dice, flip chips etc.), or partially and/or fully packaged dice.

III. Device Testing

The following operational tests illustrate the reliability experiments to test the electrical connections of the parylene substrate.

Figure 14:
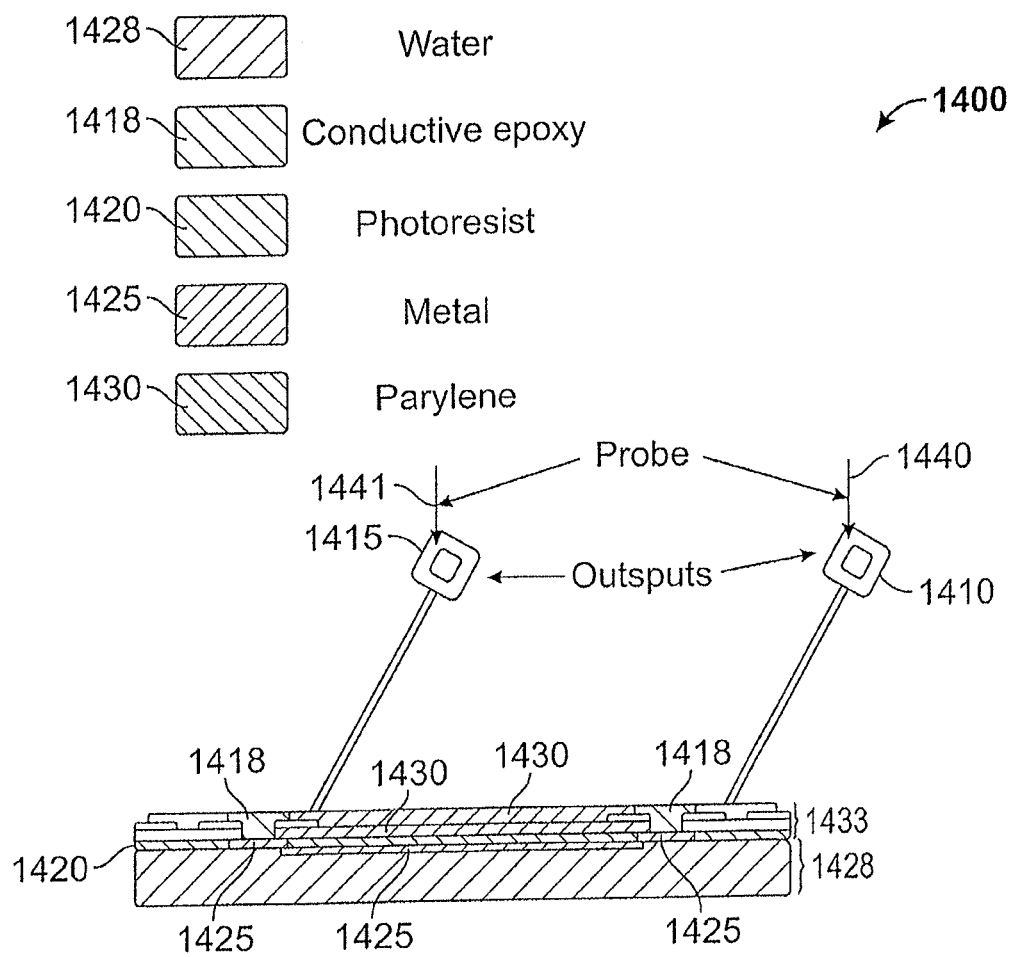
FIG. 14 shows the setup of the measurement, wherein the electrode array outputs (the electrode end that is placed on macula) were probed to check the connection.

FIG. 14 illustrates the setup 1400 for the test measurements. As shown therein, the electrode array outputs 1410, 1415 were probed to check the electrical connections. In certain aspects, these electrodes are placed on the macula of a mammalian eye such as a human eye.

The setup 1400 includes a patterned chip 1428 and a parylene interface 1433. Photoresist 1420 is sandwich between the wafer 1428 and the parylene 1430. In addition, metal 1425 is included between the wafer 1428 and the photoresist 1420, or between the conductive epoxy 1418 and the wafer. Electrically conductive vias are provided to electrically connect components (e.g., ICs/traces/contacts/passive components, etc.) that reside at different layers of the package. The vias are arranged to extend through various layers. By way of example, the vias may be used to couple traces from two different interconnect layers together; a die or another component to an interconnect layer; a contact to a trace, die or other component, etc.

In one experiment, the connection yield right after squeegee was measured by probing using 1440 and 1441, the stimulating electrodes. Afterwards, an additional thick parylene-C was coated on the entire device (except the output electrodes) to insulate and stabilize the connection, and to protect the metals embedded in the parylene-C substrate from corrosive body fluids. The connection yield was recorded after this coating. Finally, the device was soaked in 90° C. saline solution for 5 days and the connection yield was again recorded.

Figure 15:
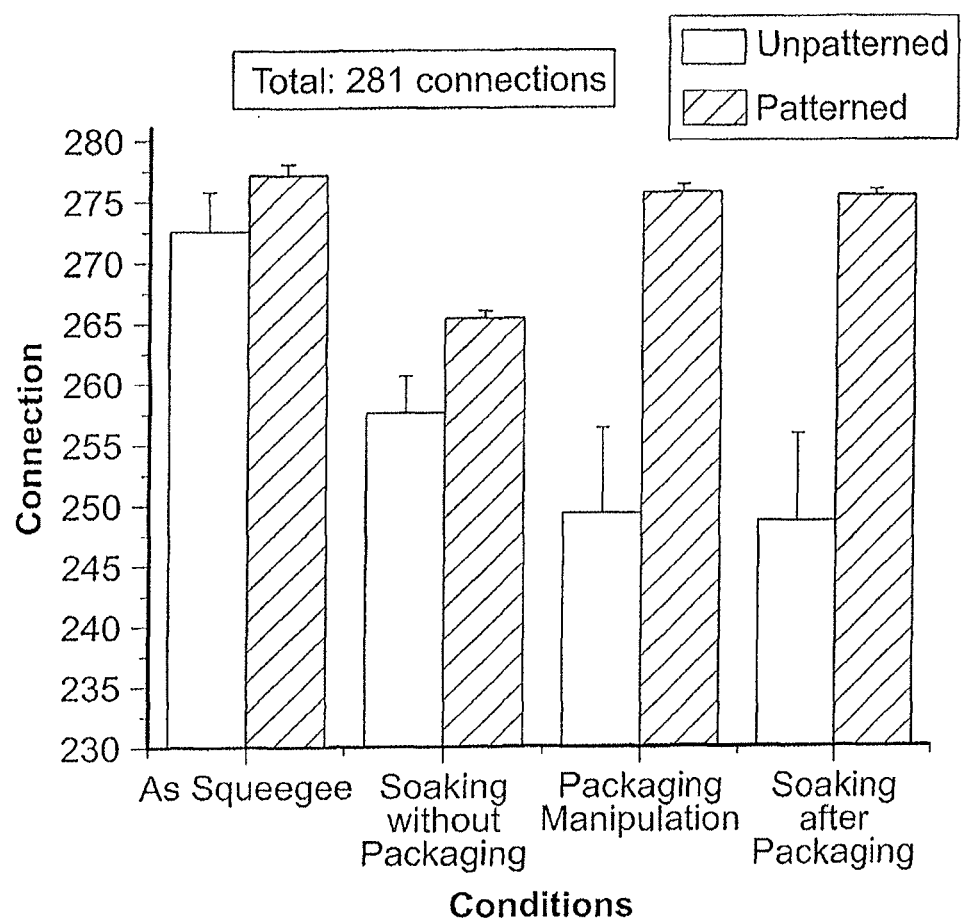
FIG. 15 shows the connection yields under 4 different conditions; reliability tests were carried out after squeegee connection, encapsulation by parylene-C coating, and accelerated soaking in 90° C. saline.

The results in FIG. 15 show that the yield in operation of the inventive device under four different conditions. Reliability tests were carried out after squeegee connection; soaking without encapsulation; encapsulation by parylene-C coating; and accelerated soaking in 90° C. saline. The results indicated that the processes combined with thick parylene-C coating for packaging does provide a high connection yield.

The results indicate that the new gluing technique is satisfactory (~98%), while the yield without the new technique is significantly lower (~88%). Moreover, for the connections without photoresist gluing techniques, most of the disconnections happened at peripheral pads where delamination force is applied.

In addition, the limits of the pad size and separation between pads were investigated. Chips with different pad separations and sizes were designed and fabricated for measurement.

Figure 16A:
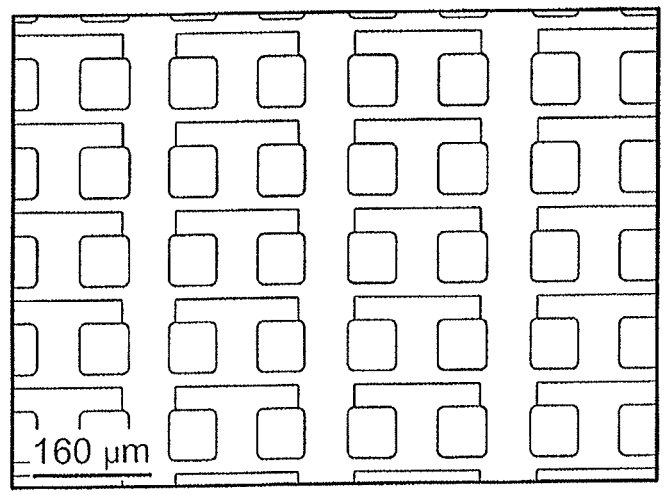
FIGS. 16A-16D show in FIG. 16A dummy chips with 40 µm by 40 µm pad size and 40 µm separation.
Figure 16B:
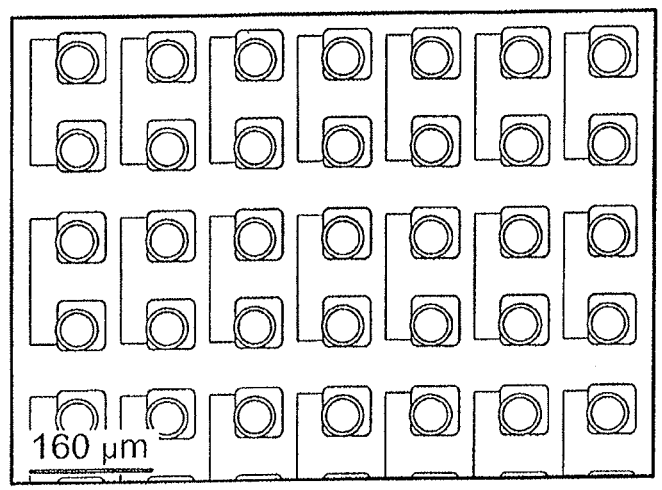
Figure 16C:
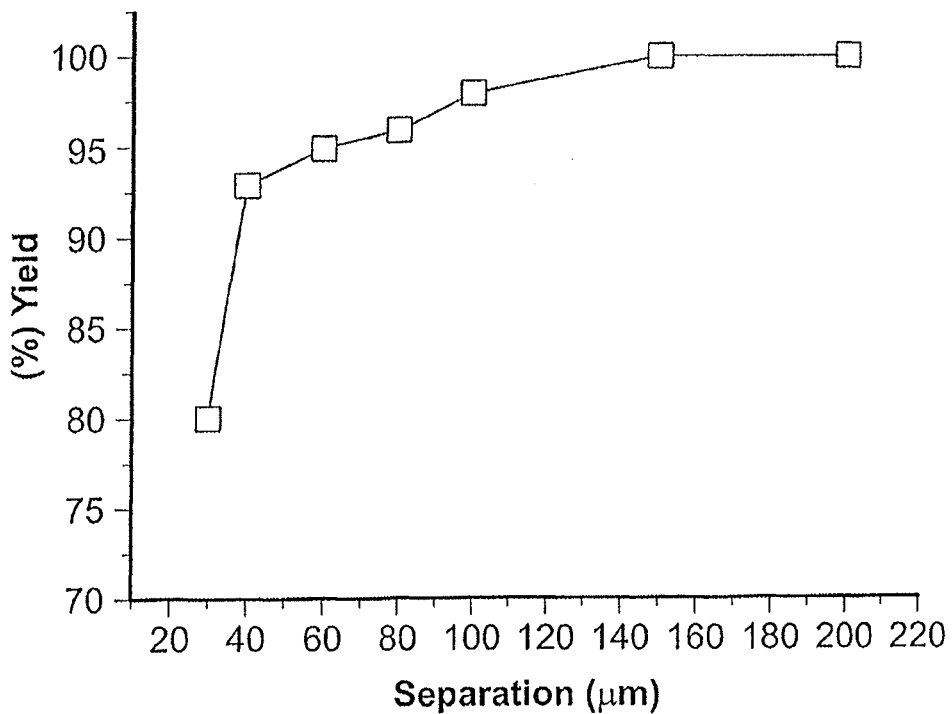
Figure 16D:
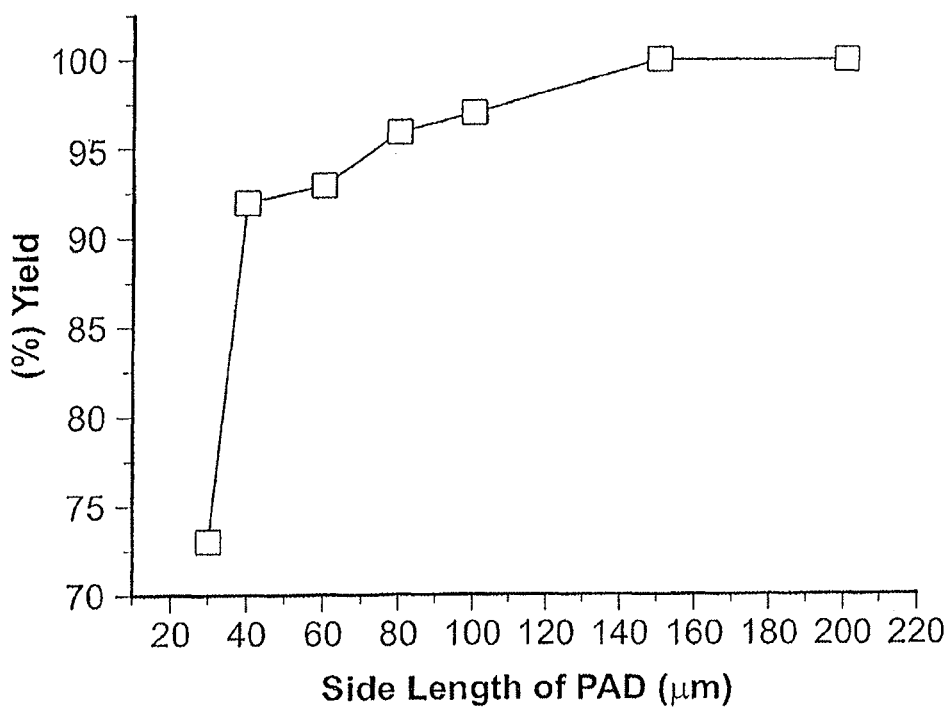

FIG. 16A shows chips with 40 μm by 40 μm pad size and 40 μm separation. FIG. 16B shows connections between parylene substrate and a chip. FIG. 16C shows yield vs separation of pads. FIG. 16D shows yield vs side length of pads. The results show that high connection yield (>90%) can be achieved for pads as small as 40 μm by 40 μm and with a 40 μm separation in between.

Based on these current results, as many as 10,000 connections within an area of 6 mm by 6 mm is achieved. This is satisfactory for current retinal prosthetic applications.

In certain other aspects, a packaging technology is designed for devices with low-density connections. As such, in another embodiment, the present invention provides:
  a biocompatible package for low density connections, comprising:
  a feedthrough layer;
  an application specific integrated circuit (ASIC) face down on the feedthrough layer;
  a printed circuit board (PCB) attached to the ASIC adapted for off-chip components and wire bonded to the feedthrough layer;
  metal walls adjacent the feedthrough layer; and a metal lid to encase and make the biocompatible package.

Figure 17:
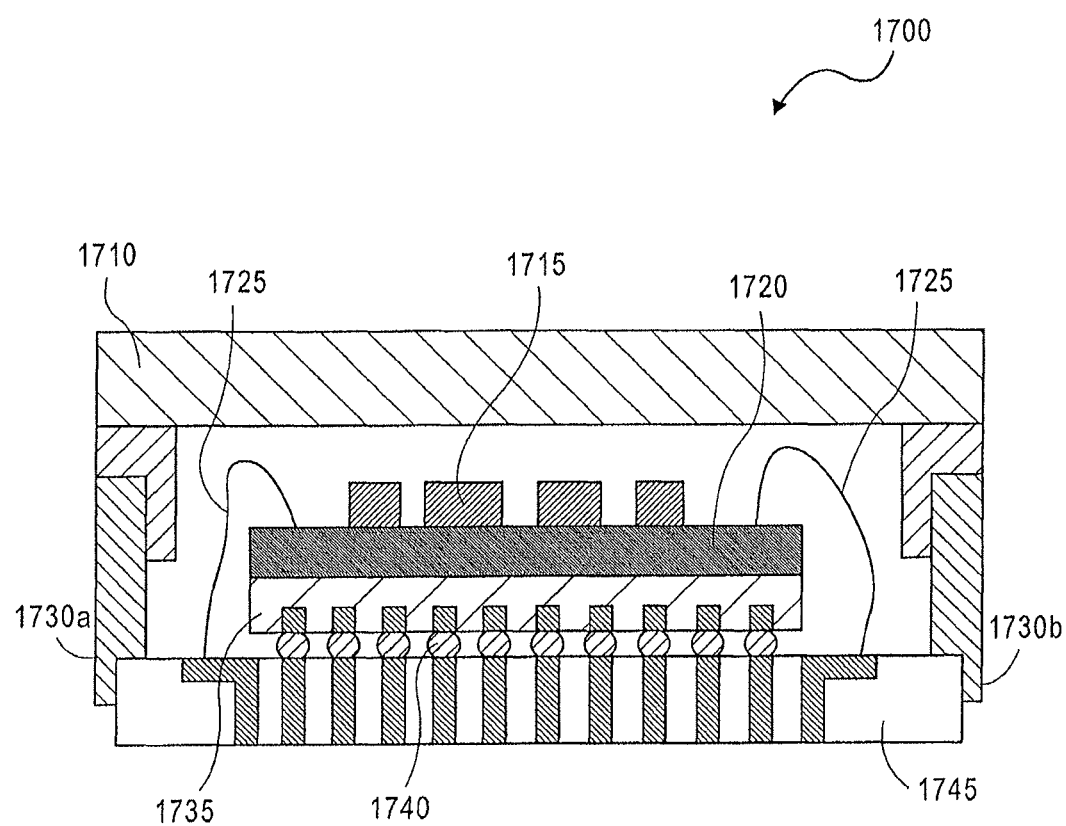
FIG. 17 shows one embodiment of a low density packaging technology.

FIG. 17 shows one embodiment of a low density packaging technology. As illustrated therein, an ASIC 1735 is placed faced down to connect with a feedthrough layer 1745 (e.g., made of ceramic or other biocompatible material) by flip-chip bonding techniques to make an electrical connection. Off-chip components 1715 are connected to a PCB 1720 by soldering or by using conductive epoxy to make an electrical connection. Then, the PCB 1720 is attached to the backside of the ASIC 1735 by a non-conductive epoxy to make a mechanical connection, and wire bonded 1725 to the feedthrough layer 1745 (e.g. ceramic) to make an electrical connection. Solder balls 1740 are used to make an electrical connection between the ASIC 1735 and the feedthrough layer 1745 by flip chip bonding.

Metal walls 1730a, 1730b are then hermetically encased with a metal lid 1710 by using laser welding techniques. As shown therein, the packaging has at least two metal walls 1730a, 1730b, which are hermetically encased with a feedthrough 1745 by for example, a brazing technique.

The unique packaging technique adopts all mature connection and encasing technologies (targets to minimize the risk) including flip-chip bonding, wire bonding, brazing, or laser welding. Advantageously, it is designed for an implanted device with a circuit to survive in corrosive body fluids. The design is for 1-100 connections, such as about 1-50, 1-40, 1-30, 1-20, 1-10 within a small nanometer or millimeter area. This is satisfactory for current retinal prosthetic applications.

A feedthrough layer 1745 serves as the interface between the enclosed circuit and a flexible electrode array. The signal can be sent from the circuit to the electrode array while the circuit can still be well protected. The ceramic feedthrough includes vias made of biocompatible metals, and the layout of vias can be designed according to the ASIC and other components. A biocompatible metal wall is first encased with the feedthrough layer by a brazing technique to form a brazing joint. The ASIC is then placed faced down to flip chip bond to the ceramic substrate. Other off-chip components 1715 can also be soldered or flip chip bonded to the ceramic substrate. Alternatively, an ASIC and an off-chip component can stay on the same plane and will occupy more area.

Another preferred option is to first solder or conductive epoxy bond off-chip components to the PCB. Then, the PCB can be attached on top of the ASIC (back side) by a non-conductive epoxy or any glue. Thereafter, an additional wire bonding connection can be made from the PCB to ceramic feedthrough to form a complete circuit. In this case (shown in FIG. 17), an ASIC and off-chip components are on different planes to save surface area. Advantageously, an enclosed circuit box with a low profile and a small surface area is designed. The final step is to hermetically enclose the metal lid 1710 with the metal wall 1730 by laser welding. Before this, a vacuum bake treatment is performed to remove moisture or other impurities to aid in the hermetic process.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A biocompatible flexible thin-film substrate for attachment of a device, which is an integrated circuit (IC) chip, the flexible thin-film substrate comprising:
  a first thin-film layer, which is made of parylene or a polymer;
  a metal adjacent to the first thin-film layer;
  a second thin-film layer made of parylene or a polymer adjacent to the metal to form a thin-film metal thin-film sandwich, wherein said second layer of thin-film has an opening, said opening having at least one electrical contact provided on an internal surface thereof, said opening configured to accept at least one electrical circuit device, which is an integrated circuit (IC) chip and to provide electrical communication between said at least one electrical contact and said at least one electrical circuit device, which is an integrated circuit (IC) chip, said biocompatible thin-film substrate configured to be implanted within a living organism after accepting said at least one electrical circuit device.

2. The biocompatible substrate of claim 1, wherein the substrate is a parylene substrate.

3. The biocompatible substrate of claim 2, wherein the first thin-film layer and the second thin-film layer are each independently selected from the group consisting of parylene, polyimide, Teflon, or Kapton.

4. The biocompatible substrate of claim 3, wherein the first thin-film layer and the second thin-film layer are each parylene.

5. The biocompatible substrate of claim 2, wherein the parylene substrate is first treated with oxygen plasma to enhancing bonding.

6. The biocompatible substrate of claim 1 wherein the device is integrated in the substrate by a conductive epoxy squeegee electrical connection.

7. The biocompatible substrate of claim 1 wherein the device is integrated into the substrate by a photo-patternable adhesive used as a mechanical glue.

8. The biocompatible substrate of claim 7, wherein the photo-patternable adhesive or epoxy is photoresist.

9. The biocompatible parylene substrate of claim 8, wherein the photoresist is a member selected from the group consisting of SU-8, AZ4620, AZ1518, AZ4400, AZ9260, THB-126N, WPR-5100, BCB, and polyimide.

10. The biocompatible substrate of claim 1, wherein the first layer has a thickness of between about 0.1 μm to about 100 μm thick.

11. The biocompatible substrate of claim 1, wherein the second layer is between 10 μm and 200 μm thick.

12. The biocompatible substrate of claim 1, wherein said parylene is a member selected from the group consisting of parylene N, C, D, HT, AM, A or combinations thereof can also be used.

13. The biocompatible substrate of claim 12, wherein said parylene is parylene-C.

14. The biocompatible substrate of claim 1, wherein said metal is a metal alloy.

15. The biocompatible substrate of claim 14, wherein said metal alloy is a member selected from the group consisting of Cr/Au, Ni/Au, Ti/Au, Al/Ti, Ag/Ti, Cr/Au/Ti/Ni/Au, Ni/Pd/Au, Ti/Ni/Au and combinations thereof.

16. The biocompatible substrate of claim 15, wherein said metal alloy is a member selected from the group consisting of Cr/Au, Ni/Au, Ti/Au, Al/Ti, Ag/Ti, Cr/Au/Ti/Ni/Au, Ni/Pd/Au, Ti/Ni/Au and combinations thereof.

17. The biocompatible substrate of claim 15, wherein said metal alloy is Ti/Au.

* * * * *